(12) United States Patent
Oyola et al.

(10) Patent No.: US 8,562,642 B2
(45) Date of Patent: Oct. 22, 2013

(54) METHOD AND APPARATUS FOR TISSUE RESECTION

(75) Inventors: Arnold E. Oyola, Northborough, MA (US); Marcia Buiser, Watertown, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 116 days.

(21) Appl. No.: 13/070,321

(22) Filed: Mar. 23, 2011

(65) Prior Publication Data

US 2011/0172691 A1   Jul. 14, 2011

Related U.S. Application Data

(62) Division of application No. 11/777,931, filed on Jul. 13, 2007, now abandoned.

(60) Provisional application No. 60/807,815, filed on Jul. 19, 2006.

(51) Int. Cl.
*A61B 17/08* (2006.01)

(52) U.S. Cl.
USPC ............................. 606/213; 606/170; 606/37

(58) Field of Classification Search
USPC ......... 606/37, 39, 40, 41, 167, 169, 170, 171, 606/213; 600/562, 564, 568, 570
See application file for complete search history.

(56) References Cited

U.S. PATENT DOCUMENTS

| | | | |
|---|---|---|---|
| 4,699,614 A | 10/1987 | Glazier | |
| 5,122,147 A | 6/1992 | Sewell, Jr. | |
| 6,033,401 A | 3/2000 | Edwards et al. | |
| 6,494,896 B1 * | 12/2002 | D'Alessio et al. | 606/213 |
| 6,565,526 B2 | 5/2003 | Seward | |
| 6,770,070 B1 | 8/2004 | Balbierz | |
| 7,083,634 B2 * | 8/2006 | Shalaby | 606/213 |
| 2001/0007069 A1 * | 7/2001 | Bombard et al. | 606/41 |

(Continued)

FOREIGN PATENT DOCUMENTS

| WO | WO 95/10328 | 4/1995 |
|---|---|---|
| WO | WO 02/054941 A2 | 7/2002 |

OTHER PUBLICATIONS

Y. Nakayama and T. Matsuda, "Photocurable Surgical Tissue Adhesive Glues Composed of Photoreactive Gelatin and Poly(Ethylene Glycol) Diacrylate," Journal of Biomedical Mater Res. (Appl Biomater), 1999; 48(4), pp. 511-521, John Wiley and Sons, Inc.

(Continued)

*Primary Examiner* — Ryan Severson
*Assistant Examiner* — Jonathan W Miles
(74) *Attorney, Agent, or Firm* — Bookoff McAndrews, PLLC (57) ABSTRACT

A resection device includes an elongated probe shaft and a tissue resection member disposed at a distal end of the elongated probe shaft. The tissue resection member has a cutting surface configured for being placed in contact with tissue. In one aspect of the invention, at least one ejection port is located adjacent to the cutting surface of the tissue resection member, wherein the at least one ejection port is coupled to a source of a polymerizable hemostasis-promoting material that is delivered to the resection site of interest. In certain embodiments, polymerization of the hemostasis-promoting material may be accelerated by application of heat, radiofrequency energy, or ultra violet light.

20 Claims, 7 Drawing Sheets

(56) References Cited

U.S. PATENT DOCUMENTS

| | | | |
|---|---|---|---|
| 2002/0165593 A1 | 11/2002 | Hayashi et al. | |
| 2004/0204728 A1 | 10/2004 | Haefner | |
| 2004/0210282 A1* | 10/2004 | Flock et al. | 607/96 |
| 2007/0156127 A1* | 7/2007 | Rioux et al. | 606/32 |
| 2008/0021486 A1 | 1/2008 | Oyola et al. | |

OTHER PUBLICATIONS

K. Ono, M. Ishihara, Y. Ozeki, H. Deguchi, Mitsuharu Sato, Y. Saito, H. Yura, Masato Sato, M. Kikuchi, a. Kurita, T. Maehara, "Experimental Evaluation of Photocrosslinkable Chotosan as a Biological Adhesive with Surgical Applications," Surgery, Nov. 2001; 130(5), pp. 844-50, Mosby, Inc.

PCT International Preliminary Report on Patentability (Chapter I of the Patent Cooperation Treaty) for PCT/US2007/073516, Applicant: Boston Scientific Scimed, Inc., Form PCT/IB/326 and 373, dated Jan. 29, 2009 (4 pages).

PCT International Search Report for PCT/US2007/073516, Applicant: Boston Scientific Scimed, Inc., Forms PCT/ISA/220 and PCT/ISA/210, dated Jan. 15, 2008 (6 pages).

PCT Written Opinion for PCT/US2007/073516, Applicant: Boston Scientific Scimed, Inc., Form PCT/ISA/237, dated Jan. 15, 2008 (6 pages).

* cited by examiner

METHOD AND APPARATUS FOR TISSUE RESECTION

RELATED APPLICATION DATA

The present application is a divisional of co-pending U.S. Application Ser. No. 11/777,931, filed Jul. 13, 2007, which claims the benefit under 35 U.S.C. §119to U.S. provisional patent application Ser. No. 60/807,815 filed Jul. 19, 2006. The foregoing applications are hereby incorporated by reference into the present application in their entirety.

FIELD OF THE INVENTION

The field of the invention generally relates to tissue resection devices and methods. More particularly, the field of the invention pertains to devices and methods for use in resecting tissue such as, for example, diseased organ tissue.

BACKGROUND OF THE INVENTION

Electrosurgery is now a widely used surgical method for treating tissue abnormalities. One class of electrosurgical abalation devices are so-called monopolar electrosurgical devices. Typically such ablation devices include an electrosurgical probe having a first or "active" electrode extending from one end. The electrosurgical probe is electrically coupled to an electrosurgical generator, which provides a high frequency electric current. A remote control or hand-activated switch is attached to the generator and commonly extends to a foot switch located in proximity to the operating theater. During an operation, a second or "return" electrode, having a much larger surface area than the active electrode, is positioned in contact with the skin of the patient (e.g., a patch). The surgeon may then bring the active electrode in close proximity to the tissue and activate the foot control switch, which causes electrical current to arc from the distal portion of the active electrode and flow through tissue to the larger return electrode.

Still other electrosurgical abalation devices are classified as bipolar-based. In these devices no return electrode is used. Instead, a second electrode is closely positioned adjacent to the first electrode, with both electrodes being attached to an electrosurgical probe. As with the monopolar-based devices, the electrosurgical probe is electrically coupled to an electrosurgical generator. When this generator is activated, electrical current arcs from the end of the first electrode to the end of the second electrode, flowing through the intervening tissue. In practice, several electrodes may be employed, and depending on the relative size or locality of the electrodes, one or more electrodes may be active.

Whether arranged in a monopolar or bipolar fashion, the active electrode may be operated to either cut tissue or coagulate tissue. When used to cut tissue, the electrical arcing and corresponding current flow results in a highly intense, but localized heating, sufficient enough to break intercellular bonds, cellular membranes, and cellular contents, resulting in tissue severance. When used to coagulate tissue, the electrical arcing results in a low level current that denatures cells to a sufficient depth without significant breakage of intercellular bonds, i.e., without cutting the tissue.

There are many medical procedures in which tissue is cut or carved away for diagnostic or therapeutic reasons. For example, during hepatic transection, one or more lobes of a liver containing abnormal tissue, such as malignant tissue or fibrous tissue caused by cirrhosis, are cut away. There exists various modalities, including mechanical, ultrasonic, and electrical (which includes RF energy), that can be used to effect the resection of abnormal tissue. Regardless of which modality is used, however, extensive bleeding can occur, which can obstruct the surgeon's view and lead to dangerous blood loss levels, requiring transfusion of blood, which increases the complexity, time, and expense of the resection procedure. To prevent extensive bleeding, hemostatic mechanisms, such as blood inflow occlusion, coagulants (e.g., Surgicel™ or Tisseel™), and energy coagulation (e.g., electrosurgical coagulation or argon-beam coagulation), can be used.

In the case where an electrosurgical coagulation means is used, the bleeding can be treated or avoided by coagulating the tissue in the treatment areas with an electro-coagulator that applies a low level current to denature cells to a sufficient depth without breaking intercellular bonds, i.e., without cutting the tissue. Because of their natural coagulation capability, ease of use, and ubiquity, electrosurgical modalities are often used to resect tissue.

During a typical electrosurgical resection procedure, electrical energy can be conveyed from an electrode along a resection line in the tissue. The electrode may be operated in a manner that incises the tissue along the resection line, or coagulates the tissue along the resection line, which can then be subsequently dissected using the same coagulation electrode or a separate tissue dissector to gradually separate the tissue. In the case where an organ is resected, application of RF energy divides the parenchyma, thereby skeletonizing the organ, i.e., leaving vascular tissue that is typically more difficult to cut or dissect relative to the parenchyma.

When a blood vessel is encountered, RF energy can be applied to shrink the collagen contained in the blood vessel walls, thereby closing the blood lumen and achieving hemostasis. The blood vessel can then be mechanically transected using a scalpel or scissors without fear of blood loss. In general, for smaller blood vessels less than 3 mm in diameter, hemostasis may be achieved within 10 seconds, whereas for larger blood vessels up to 5 mm in diameter, the time required for hemostasis may increase to 15-20 seconds. During or after resection of the tissue, RF energy can be applied to any "bleeders" (i.e., vessels from which blood flows or oozes) to provide complete hemostasis for the resected organ. This may be accomplished by employing the same device used for cutting.

When electrosurgically resecting tissue, care must be taken to prevent the heat generated by the electrode from charring the tissue, which generates an undesirable odor, results in tissue becoming stuck on the electrosurgical probe, and most importantly, increases tissue resistance, thereby reducing the efficiency of the procedure. Adding an electrically conductive fluid, such as saline, to the electrosurgery site reduces the temperature of the electrode and keeps the tissue temperature below the water boiling point (100° C.), thereby avoiding smoke and reducing the amount of charring. The electrically conductive fluid can be provided through the probe that carries the active electrode or by another separate device.

Although the application of electrically conductive fluid to the electrosurgery site generally increases the efficiency of the RF energy application, energy applied to an electrode may rapidly diffuse into fluid that has accumulated and into tissue that has already been removed. As a result, if the fluid and removed tissue is not effectively aspirated from the tissue site, the electrosurgery may either be inadequately carried out, or a greater than necessary amount of energy must be applied to the electrode to perform the surgery. Increasing the energy used during electrosurgery increases the chance that adjacent healthy tissues may be damaged. At the same time that fluid accumulation is avoided, care must be taken to ensure that fluid is continuously flowed to the tissue site to ensure that tissue charring does not take place. For example, if flow of the fluid is momentarily stopped, e.g., if the tube supplying the fluid is kinked or stepped on, or the port on the fluid delivery device becomes clogged or otherwise occluded, RF energy may continue to be conveyed from the electrode, thereby resulting in a condition where tissue charring may occur.

A related concern with existing electrosurgical ablation devices is that heat generated at the application site rapidly dissipates away from the treated area of interest. It is preferable, however to localize the elevated temperatures (and coagulation effect) to the application site. Heat energy that is dissipated away from the application site has the potential to damage or destroy healthy tissue. In addition, heat dissipation requires that additional energy be applied to the electrode which, as stated above, increases the probability that adjacent healthy tissues may be damaged or destroyed.

While electrosurgical resection of tissue reduces the amount of blood loss, as compared to other tissue resection modalities, it still involves a tedious process that includes painstakingly cutting/dissecting through the parenchyma and ligating and cutting through blood vessels. Moreover, because time is of the essence in such procedures there is a need to reduce the amount of time wasted in manipulating and switching between multiple instruments. It is generally desirable to provide as much functionality in a single device to avoid the use of multiple devices having separate functions. Similarly, the use of multiple devices often requires one or more surgeons or other trained personnel to assist.

There remains a need for resection devices and methods that can be used to efficiently resect vascularized tissue. Similarly, there is a need for such devices and methods to effectuate and maintain hemostasis at the treatment site. There is also a need for resection methods and devices that reduce or eliminate the need for a physician to switch between different surgical instruments.

SUMMARY OF THE INVENTION

In one embodiment of the invention, a resection probe is provided that includes cutting capability as well as the means to effectuate or maintain hemostasis at the cut site. Hemostasis may be maintained or otherwise controlled by the use of polymerizable hemostasis-promoting material that is delivered at or near a distal end of the resection probe. Polymerization of the hemostasis-promoting material may be initiated or accelerated by application of heat, radiofrequency energy, or ultra violet light delivered in situ by the probe.

In one particular aspect of the invention, the resection device includes an elongated shaft and a tissue resection member disposed at a distal end of the elongated probe shaft that includes a cutting surface configured for being placed in contact with tissue. At least one ejection port is located adjacent to the cutting surface of the tissue resection member and is coupled to a source of polymerizable hemostasis-promoting material.

The polymerizable hemostasis-promoting material may be formed from a thermally-activated polymer, a light-activated polymer (e.g., ultra violet light), or energy-activated polymer (e.g., radiofrequency (RF) energy).

In certain embodiments, the tissue resection member may take the form of a resection electrode that cuts tissue in response to an applied RF signal. In still other embodiments, the tissue resection member may be formed from a mechanical resection member. As one example, the mechanical resection member may be formed as a blade or knife. In still another aspect of the invention, the tissue resection member may be formed from a vibrational cutting member. In still another aspect, the tissue resection member is formed from a laser.

In still another aspect of the invention, the polymerizable hemostasis-promoting material may be under pressure when delivered via the one or more ejection ports. A valving mechanism or the like may be used to selectively dispense the material to the site of interest. In certain embodiments, the dispensing of the hemostasis-promoting material to the site of interest may be synchronized with the cutting operation of the tissue resection member. For example, the hemostasis-promoting material may be dispensed to the site of interest when the tissue resection member cuts or touches the tissue.

In yet another embodiment of the invention, an elongated surgical probe is provided that includes an elongated probe shaft and a tissue resection member disposed at a distal end of the elongated probe shaft, the tissue resection member having a cutting surface configured for being placed into contact with the tissue. In this embodiment, a porous delivery member is disposed at the distal end of the elongated probe shaft and is coupled to a source of polymerizable hemostasis-promoting material. In one exemplary embodiment, the porous delivery member may be formed from a medical-grade sponge.

As in the embodiments described above, various activating mechanisms may be employed to activate the hemostasis-promoting material. These include, by way of example, thermally-activated, light-activated, and energy-activated compounds. Similarly, various tissue resection members may be used to cut the tissue site of interest.

According to some embodiments of the invention, the tissue resection member is formed as a resection electrode. In such an embodiment, an insulating member may be interposed between the resection electrode and the porous delivery member. In addition, the resection electrode and the porous delivery member may be in electrical contact with one another in either a monopolar or bipolar arrangement.

In still another aspect of the invention, a resection device includes an elongated probe shaft and a tissue resection member disposed at a distal end of the elongated probe shaft. The tissue resection member includes a cutting surface configured for being placed into contact with tissue. A porous delivery member is disposed at the distal end of the elongated probe shaft and is coupled to a source of polymerizable hemostasis-promoting material. An ultra violet light emitter is located adjacent to the porous delivery member. In order to prevent polymerization of the hemostasis-promoting material within porous delivery member, a light shield is interposed between the porous delivery member and the ultra violet light emitter.

In yet another aspect of the invention, a method of resecting tissue includes providing a resection device of the type described above. Using the probe, the tissue is cut with the cutting surface of the tissue resection member. In addition, the polymerizable hemostasis-promoting material is ejected or otherwise delivered from the one or more ejection ports and comes into contact with at least a portion of the cut tissue. In an alternative aspect of the invention, the polymerizable hemostasis-promoting material is delivered to the resection site via the porous delivery member.

In one aspect of the invention, the polymerizable hemostasis-promoting material that is located on the cut tissue is then activated or cured. The curing or activation process may be accelerated or initiated by the application of heat, ultra violet radiation, or RF energy from the resection device. In certain embodiments of the invention, the polymerizable hemostasis-promoting material is ejected or effused from the at least one ejection port at substantially the same time the tissue is cut by the resection device. In an alternative aspect of the invention, the polymerizable hemostasis-promoting material is ejected or effused from the at least one ejection port after the tissue is cut.

It is thus one object of the invention to provide a resection device that is capable of resecting tissue while minimizing or preventing the bleeding from the cut tissue. It is another object of the invention to provide a device is able to localize coagulative heating to a relatively small site of interest. Related to this, it is a further object of the invention to provide a resection device that reduces heat dissipation into tissue surrounding a cut region. It is yet another object of the invention to provide a single device that is capable of cutting tissue and promoting hemostasis at the same time. Further features and advantages will become apparent upon review of the following drawings and description of the preferred embodiments.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1A is plan view of the distal end of the resection device illustrated in FIG. 1. FIG. 1A illustrates a lumen in phantom (dashed lines) that is coupled to the ejection ports of the probe.

FIG. 1B is a plan view of a distal end of a resection device according to another aspect of the invention. FIG. 1B illustrates a single ejection port in the form of a slit. Also shown in FIG. 1B in phantom is a lumen coupled to the single ejection port.

FIG. 2A is plan view of the distal end of the resection device illustrated in FIG. 2. FIG. 2A illustrates a lumen in phantom (dashed lines) that is coupled to the ejection ports of the probe.

FIG. 2B is a plan view of a distal end of a resection device according to another aspect of the invention. FIG. 2B illustrates a single ejection port in the form of a slit. Also shown in FIG. 2B in phantom is a lumen coupled to the single ejection port.

FIG. 2D illustrates a resection device according to one embodiment of the invention. FIG. 2D illustrates a dual-chambered syringe coupled to the probe device. A portion of the shaft is shown in cross-section to illustrate the multiple conduits or lumens. A mixing port is located just proximal of the ejection ports.

FIG. 5B is a perspective view of the tissue of FIG. 5A showing a partially-cut tissue. As seen in FIG. 5A, the tissue is cut generally along a resection line.

FIG. 5C is a perspective view of the tissues of FIGS. 5A and 5B showing fully-cut tissue. As seen in FIG. 5C, the tissue has been resected into a healthy portion (left) and an unhealthy portion (right).

DETAILED DESCRIPTION OF THE PREFERRED EMBODIMENTS

Figure 1:
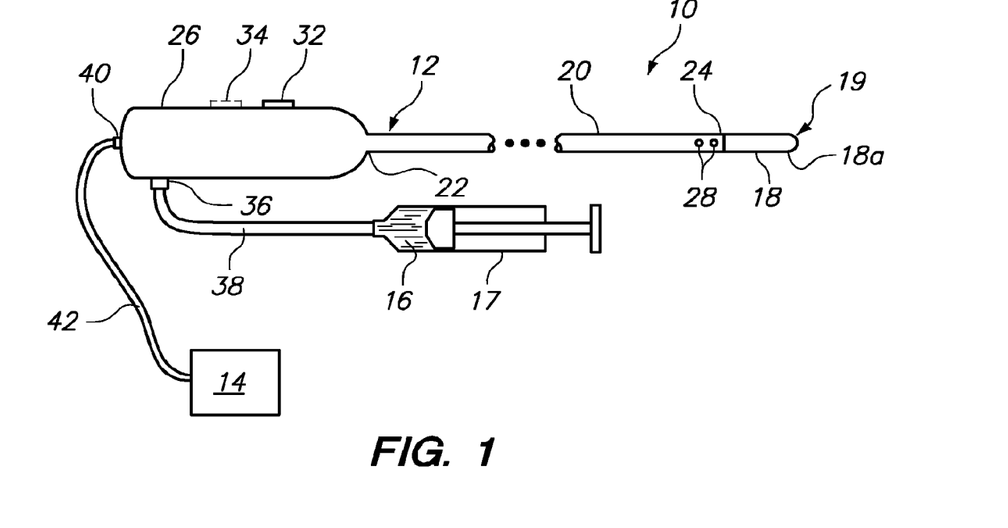
FIG. 1 is a plan view of a resection device according to one preferred aspect of the invention.

FIG. 1 illustrates a tissue resection device 10 constructed in accordance with one embodiment of the present invention. In this embodiment, the tissue resection device 10 generally includes a resection device or probe 12 configured for resecting and coagulating tissue and a syringe 17 or other pumping source configured for delivering a polymerizable hemostasis-promoting material 16 to the resection site. The resection probe 12 includes a tissue resection member 18 disposed on a distal end of the resection probe 12 that is configured for being placed into contact with tissue.

In the embodiment illustrated in FIG. 1, tissue resection member 18 is formed as a resection electrode 19. Accordingly, the device 10 further includes an ablation energy source, and in particular a radio frequency (RF) or microwave generator 14, configured for supplying RF energy or microwave energy to the resection electrode 19 in a controlled manner.

The resection probe 12 generally comprises an elongated probe shaft 20 having a proximal end 22, a distal end 24, a handle assembly 26 mounted to the proximal shaft end 22, a tissue resection member 18 mounted to the distal shaft end 24, one or more ejection ports 28 formed in the distal end 24 of the probe shaft 20, and a fluid conduit 30 (shown in phantom in FIGS. 1A, 1B) extending through the probe shaft 20 between the proximal shaft end 22 and terminating at the one or more ejection ports 28. In the illustrated embodiment, the probe shaft 20 is rigid, thereby providing maximum control at the distal end 24 of the probe shaft 20. The probe shaft 20 is composed of a suitable material, such as plastic, metal or the like, and has a suitable length, typically in the range from about 2 cm to about 30 cm, and preferably from about 10 cm to about 20 cm.

In certain embodiments, the probe shaft 20 may be formed from an electrically conductive material, in which case, the probe shaft 20 is preferably covered with an insulative material (not shown). In certain embodiments where the tissue resection member 18 may be selectively activated or energized (e.g., a resection electrode), the handle assembly 26 may include one or more activating switches or buttons 32 which can be used to selectively energize the tissue resection member 18. In still other embodiments, the handle assembly 26 may include another switch or button 34 that controls or modulates the dispensing of the polymerizable hemostasis-promoting material 16 from the syringe 17. For example, the syringe 17 or other pumping device may be coupled to a pumping source that may be selectively activated via the button 34. In still another embodiment, the button 34 may be operably connected to a valve or the like (not shown) that opens upon actuation.

The tissue resection member 18 has a cutting surface 18a, which is straight or rectilinear, so that it can be placed along a resection line. The tissue resection member 18 may be formed as a resection electrode 19 as is shown, for example, in FIGS. 1, 1A, 1B, 3, 3A, 3B, 4, 4A, and 4B. In embodiments utilizing a resection electrode 19 as the tissue resection member 18, tissue separation may be achieved by conveying electrical energy to or from the resection member 18 to either cut the tissue or coagulate the tissue. If the resection member 18 operates to coagulate the tissue, the mechanical pressure applied by the resection member 18 may naturally separate the tissue as it is coagulated. As will be described in further detail below, electrical energy can either be conveyed from the resection electrode 19 in a monopolar mode or a bipolar mode.

Figure 2:
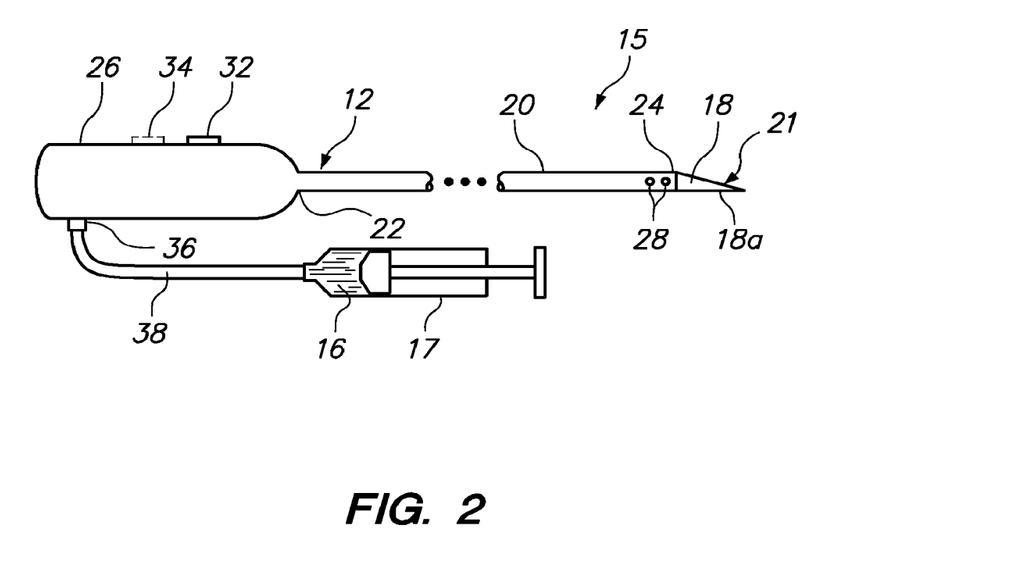
FIG. 2 is a plan view of a resection device according to another preferred aspect of the invention.
Figure 2A:
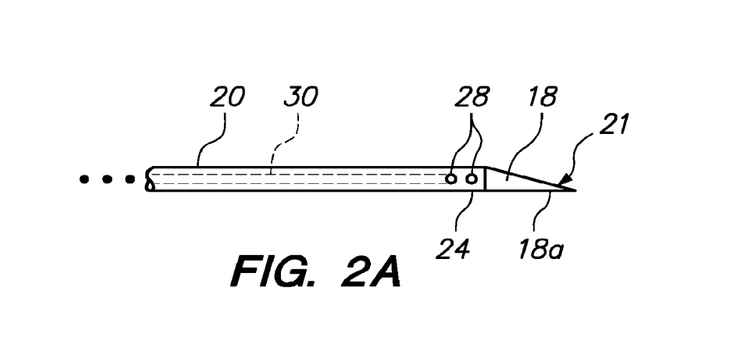
Figure 2B:
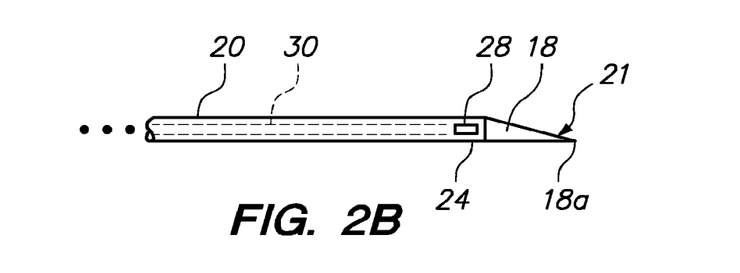

With reference to FIGS. 2, 2A, 2B, in an alternative configuration, the tissue resection member 18 may be formed from a mechanical resection member 21, which means that tissue separation may be achieved by mechanically manipulating the tissue with the resection member 18. For example, FIGS. 2, 2A, and 2B illustrate an embodiment of a device 15 in which the tissue resection member 18 is formed as a mechanical resection member 21. The mechanical resection member 21 may be formed as a blade, as is shown in FIGS. 2, 2A, and 2B. In still other embodiments, the mechanical resection member 21 may be formed as a vibrational cutting member such as, for instance, an ultrasonic knife or the like.

In this embodiment, the one or more ejection ports 28 are located adjacent to the mechanical resection member 21. FIGS. 2A and 2B illustrate the ejection ports 28 being located proximal with respect to the cutting surface 18a of the blade. The ejection ports 28 may be dimensioned so as to allow the hemostasis-promoting material 16 to weep onto the cut or resected tissue. Depending on the orientation of the device 15, the hemostasis-promoting material 16 may weep or eject first onto the cutting surface 18a of the blade and then transfer to the resected tissue.

The tissue resection member 18 may optionally comprise a radiation source such as, for example, a laser (not shown). In this regard, a directed beam of radiation capable of ablating or destroying tissue may be used to resect the tissue of interest.

Figure 1A:
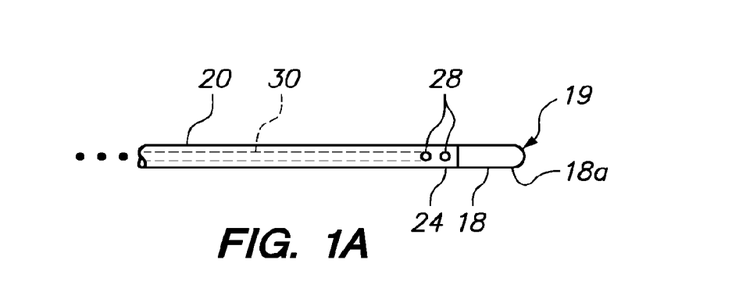
Figure 1B:
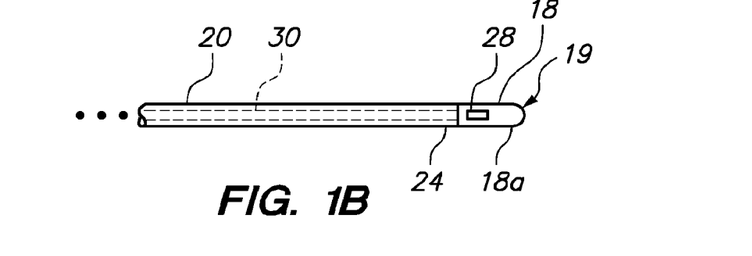

Referring back to FIGS. 1, 1A, and 1B, one or more ejection ports 28 are disposed adjacent to the cutting surface 18a of the tissue resection member 18. In the embodiment illustrated in FIG. 1A, the one or more ejection ports 28 are located proximal to the cutting surface 18a on the probe shaft 20. It is possible, however, to integrate the ejection ports 28 directly into the tissue resection member 18 as is shown, for example, in FIG. 1B. As best seen in FIGS. 1A and 1B, a fluid conduit 30 is disposed along at least a portion of the length of the probe shaft 20 and provides a lumen or passage through which the polymerizable hemostasis-promoting material 16 passes. The fluid conduit 30 is coupled at a proximal end to a port 36 or the like which can be coupled to the syringe 17 via tubing 38 or the like. The distal end of the fluid conduit 30 terminates at the one or more ejection ports 28. In this regard, the polymerizable hemostasis-promoting material 16 can flow from the syringe 17, down through the probe shaft 20, and be delivered in situ adjacent to the site of resection.

The polymerizable hemostasis-promoting material 16 may be formed as a one-component material or, alternatively, as a multi-component material. For example, in certain embodiments, the hemostasis-promoting material 16 begins to polymerize in response to outside stimulus. For instance, the hemostasis-promoting material 16 may polymerize upon application of heat (e.g., thermally-activated polymer), upon application of radiation or light (e.g., light-activated polymer), or upon application of energy such as radiofrequency (RF) or microwave energy. In another embodiment, an applied external stimulus (e.g., heat, light, RF or microwave energy) may be used to accelerate the rate of polymerization.

Figure 2C:
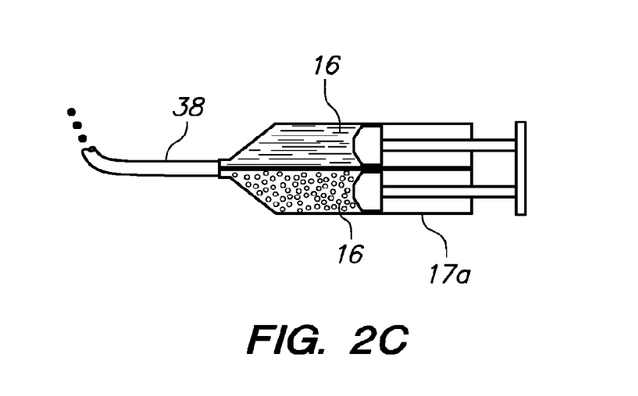
FIG. 2C illustrates a dual-chamber syringe according to one embodiment of the invention.
Figure 2D:
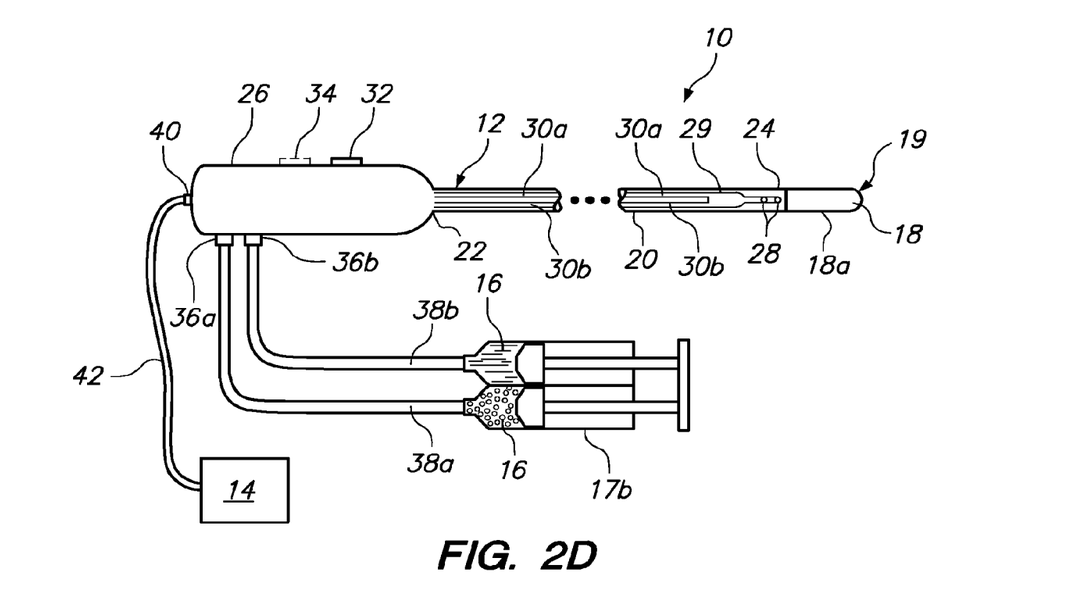

Alternatively, the hemostasis-promoting material 16 may be formed from multiple pre-polymer components that are mixed immediately before delivery to the resection site. For instance, as seen in FIGS. 2C and 2D, a two-component pre-polymer solution may be loaded into the syringe 17a, 17b just prior to the resection procedure. The material 16 has a set or cure rate that is slow-enough such that the material 16 does not solidify and occlude the conduit 30 and/or tubing 38. In one embodiment, as illustrated in FIG. 2C, a two-chamber chamber syringe 17a is provided with each chamber containing one of the two pre-polymer components. The pre-polymers are mixed together upon exit from the syringe 17a and passage into the tubing 38.

FIG. 2D illustrates another embodiment wherein a two-chamber syringe 17b is coupled at an outlet to two separate tubing conduits 38a, 38b. The two tubing conduits 38a, 38b then connect to two separate ports 36a, 36b on the probe 12. Of course a single piece tubing 38 with dual lumens may also be used. Each port 36a, 36b is coupled to a separate fluid conduits 30a, 30b traversing the length of the probe shaft 20 until terminating at or proximal to the ejection ports 28. The separate fluid conduits may be coupled to separate ejection ports 28. In this regard, the mixing of the pre-polymer components occurs external to the probe 12. Alternatively, as shown in FIG. 2D, the fluid conduits may terminate just prior to the ejection ports 28 into a mixing chamber 29 located within the probe shaft 20. The mixing chamber 29 may be formed from a common chamber or reservoir that is used to mix the pre-polymer components just prior to ejection from the probe 12. The mixing chamber 29 may be constructed of a geometry or include tortuous pathways to promote mixing of the pre-polymer components.

The hemostasis-promoting material 16 may be formed from a biocompatible or biodegradable material. As one example, the hemostasis-promoting material 16 may be formed as a polymerizable hydrogel. The hemostasis-promoting material 16 may also be formed as a curable glue or epoxy that is biocompatible or biodegradable. In embodiments where radiation such as UV light is used to initiate or accelerate polymerization, the hemostasis-promoting material 16 may be formed from a photosensitive glue or adhesive. The photosensitive glue or adhesive may also require the addition of one or more photoinitiators which may be included or loaded into the syringe 17.

Figure 5A:
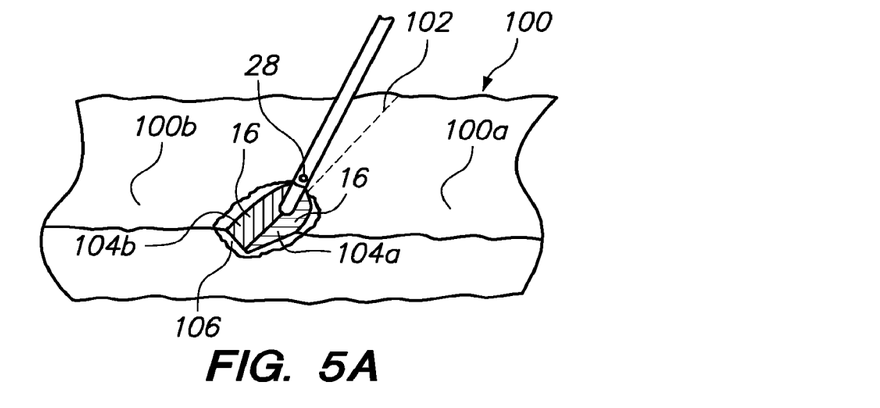
FIG. 5A is a perspective view of tissue having an unhealthy tissue portion that is shown being resected from a healthy tissue portion through use of a resection device of the type disclosed herein.
Figure 5B:
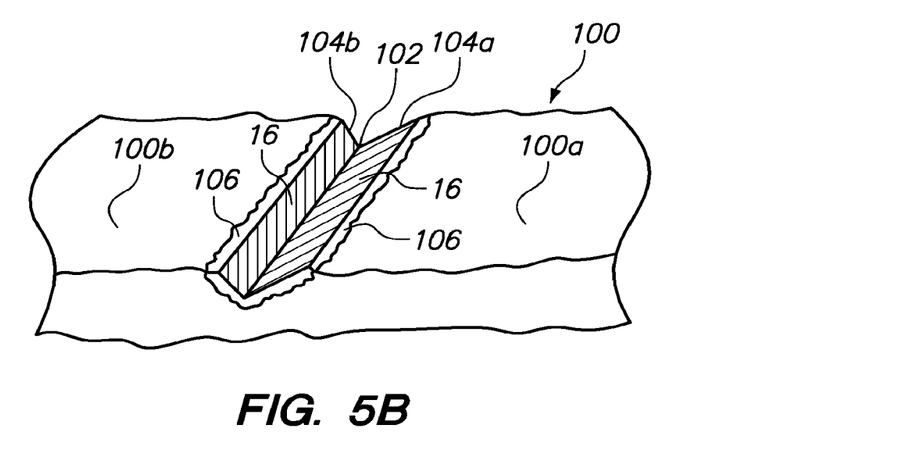
Figure 5C:
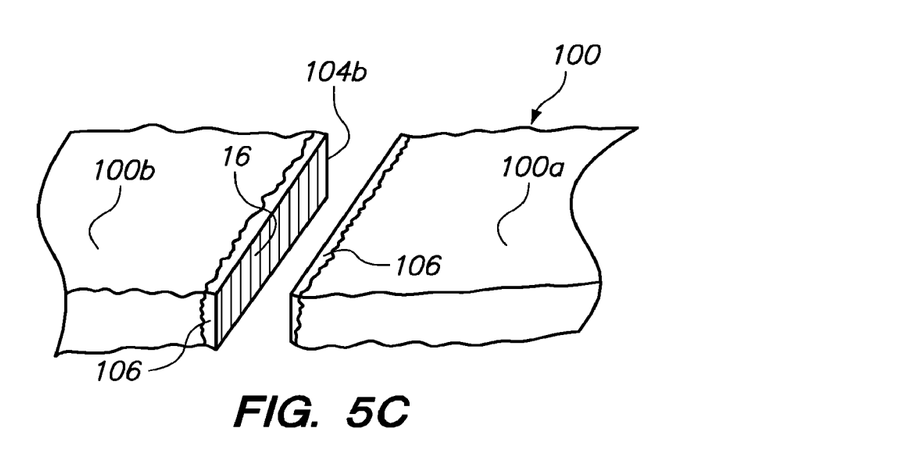

As one exemplary hemostasis-promoting material 16, a photoreactive gelatin and a water-soluble difunctional macromer (poly(ethylene glycol) diacrylate: PEGDA) may be irradiated by UV light (or even visible light) to form a gel or glue-like consistency that strongly adheres to tissue (e.g., to walls 104a, 104b as shown in FIGS. 5A-5C). The hemostasis-promoting material 16 referred to above is described in detail in Nakayama et al., *Photocurable Surgical Tissue Adhesive Glues Composed of Photoreactive Gelatin and Poly(ethylene glycol) Diacrylate*, J. Biomed Mater Res. 1999;48(4):511-521 which is incorporated by reference as if set forth fully herein. Another exemplar hemostasis-promoting material 16 may be a photocrosslinkable chitosan molecule that is curable in the presence of UV radiation. For example, the chitosan-based hydrogel disclosed in Ono et al., *Experimental Evaluation of Photocrosslinkable Chitosan as a Biologic Adhesive With Surgical Applications*, Surgery, 2001 November;130(5):844-850 may be used. The above-identified publication is incorporated by reference as if set forth fully herein.

In one embodiment, the hemostasis-promoting material 16 is delivered as a viscous or semi-viscous solution such that the material 16 readily adheres to the exposed or cut surface of tissue. Alternatively, the hemostasis-promoting material 16 may be delivered in a non-viscous state that rapidly turns viscous or semi-viscous, for example, after application of heat, light, or RF or microwave energy. The hemostasis-promoting material 16, when delivered to the resection site, advantageously forms a film or barrier on the exposed or cut surface of tissue.

In one embodiment, the hemostasis-promoting material 16 has the ability to retain heat to promote the local coagulation of tissue. For example, when used in connection with applied RF energy, the hemostasis-promoting material 16 retains heat at or adjacent to the resection site to promote localized coagulation of tissue. In this regard, dissipation of heat energy into surrounding healthy tissue is reduced. This also advantageously reduces the amount the energy needed to achieve tissue coagulation.

Referring back to FIGS. 1, 1A, and 1B, the resection probe 12 may operate in either a monopolar mode or a bipolar mode. In the monopolar mode, RF current is delivered from the RF generator 14 to the resection electrode 19, which means that current will pass from the respective electrode 19, which is configured to concentrate the energy flux in order to have an injurious effect on the surrounding tissue, and a dispersive electrode (not shown), which is located remotely from the electrode and has a sufficiently large area (typically 130 cm$^2$ for an adult), so that the current density is low and non-injurious to surrounding tissue. In the illustrated embodiment, the dispersive electrode may be attached externally to the patient, e.g., using a contact.

In a bipolar mode, the RF current is delivered between two electrodes, with one of the electrodes being the "positive" electrode element and the other of the electrodes being the "negative" electrode element. One of the electrodes may be formed from the resection electrode 19. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrode arrangements are generally more efficient than monopolar electrode arrangements.

Additionally, bipolar arrangements are generally safer for the physician and patient, since there is an ever-present danger that the physician and patient may become a ground in the monopolar arrangement, resulting in painful burns. The embodiment illustrated in FIGS. 3, 3A, and 3B, for instance, may be implemented in either a monopolar or bipolar arrangement.

Referring back to FIGS. 1, 1A, and 1B, the handle assembly 26 is composed of any suitable rigid material, such as, e.g., metal, plastic, or the like. The handle assembly 26 carries a port 36, which is in fluid communication with the fluid delivery conduit 30. In embodiments where the tissue resection member 18 is formed as a resection electrode 19, the handle assembly 26 further carries an electrical connector 40 that is electrically coupled to the resection electrode 19 via the probe shaft 20. In this case, the core of the probe shaft 20 is composed of an electrically conductive material, such as stainless steel, and the exterior of the probe shaft 20 is coated with an electrically insulative material (not shown).

Alternatively, the electrical connector 40 may be electrically coupled to the resection electrode 19 via wires (not shown) extending through the probe shaft 20 and terminating within the resection electrode 19 or in the shaft distal end 24 (which will be electrically conductive in this case) on which the resection electrode 19 is directly mounted.

The RF generator 14 is electrically connected to the electrical connector 40 on the probe 12 via a cable 42. The RF generator 14 may be a conventional RF power supply that operates at a frequency in the range from 200 KHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, operate at higher voltages and powers than would normally be necessary or suitable for tissue coagulation and/or cutting. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000 (100 W) and RF3000 (200 W). Optionally, the RF generator 14 may include means for conveying the RF energy in a "coagulation mode" or a "cutting mode." As previously described, operating an RF generator in a coagulation mode will tend to create a tissue coagulation effect, while operating an RF generator in a cutting mode will tend to create a tissue cutting effect, although tissue coagulation or cutting will ultimately depend, to a greater extent, on the structure of the electrode to or from which the electrical energy is conveyed.

Figure 3:
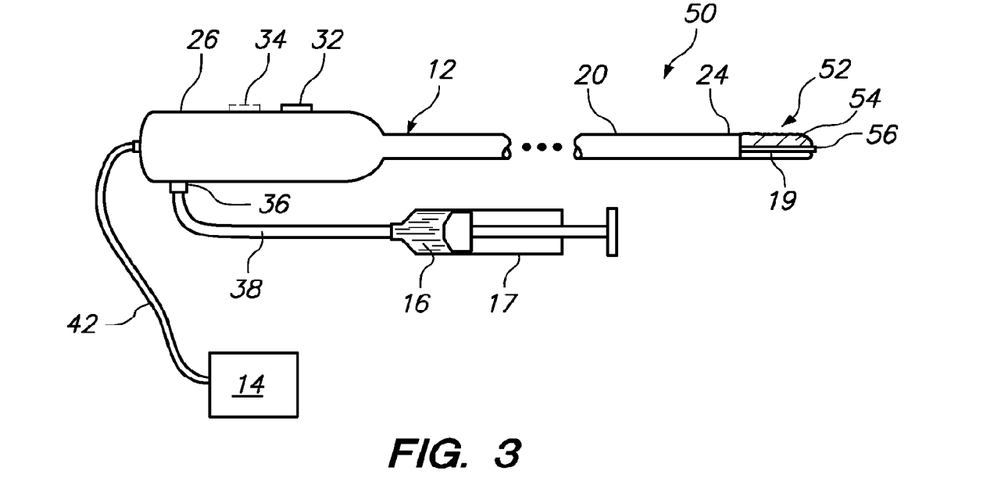
FIG. 3 is a plan view of a resection device according to another preferred aspect of the invention.
Figure 3A:
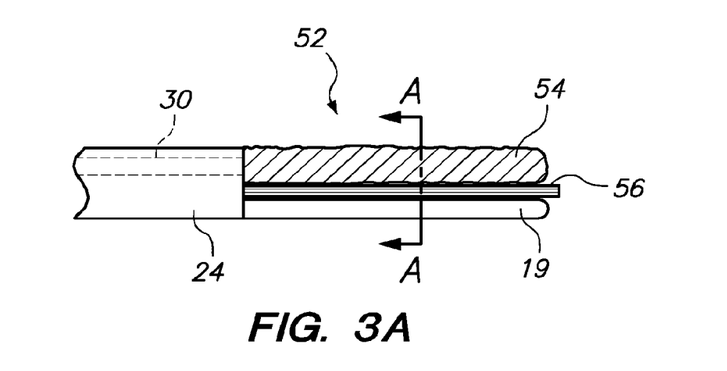
FIG. 3A is a magnified plan view of the distal end of the resection device illustrated in FIG. 3.
Figure 3B:
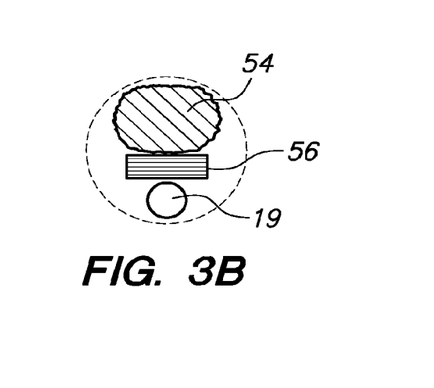
FIG. 3B is a cross-sectional view of the distal end of the resection device taken along the line A-A in FIG. 3A.

FIGS. 3, 3A, and 3B illustrate a resection probe 50 according to an alternative aspect of the invention. Those features of the resection probe 50 that are common with the embodiment illustrated in FIGS. 1, 1A, and 1B retain the same element number for sake of clarity. In this embodiment, the distal end 24 of the probe shaft 20 terminates in a tissue resection assembly 52. The assembly 52 includes a resection electrode 19 and a porous delivery member 54 separated from one another via an insulating member 56. The insulating member 56 is formed from an electrically non-conductive material and acts to electrically isolate the resection electrode 19 from the porous delivery member 54.

As best seen in FIG. 3A, the porous delivery member 54 is coupled at a proximal end to the fluid conduit 30. The porous delivery member 54 is thus in fluidic contact with the hemostasis-promoting material 16 during operation of the device 50. Suitable materials that can be used to construct the porous delivery member 54 include open-cell foam (such as polyethylene foam, polyurethane foam, polyvinylchloride foam) and medical-grade sponges. Polyvinyl alcohol (PVOH) sponges, such as Merocel™, marketed by Medtronic, Inc., and cellulose sponges, such as Weckcel™ are also suitable. It should be appreciated that material, other than foam or sponges, may be used for the porous delivery member 54 as long as it is capable of deploying a sufficient amount of hemostasis-promoting material 16. For example, spun-laced polyester, cotton, gauze, cellulose fiber, ceramic, metal (e.g., compressive metal) or the like can be used.

In one aspect of the invention, the porous delivery member 54 is used to apply or "paint" a film of hemostasis-promoting material 16 on resected tissue. For example, the porous delivery member 54 may be sized such that the stroking motion utilized in resection operations causes the porous delivery member 54 to physically contact resected tissue (e.g., as shown in FIG. 6C). Physical contact between the tissue and the porous delivery member 54 causes a layer or film to be applied to the contacted surface.

The device 50 illustrated in FIGS. 3, 3A, and 3B may be configured in either a monopolar or bipolar configuration. In the monopolar configuration, the resection electrode 19 acts as one electrode while a second or "return" electrode having a much larger surface area than the active electrode, is positioned in contact with the skin of the patient. Alternatively, in the bipolar configuration, the resection electrode 19 acts as one electrode while the porous delivery member 54 acts as the second electrode.

In the bipolar configuration, both the resection electrode 19 and the porous delivery member 54 (the second electrode) need to be in contact with tissue to complete the circuit. Gentle downward pressure placed on the probe 12, however, will cause a depression (or cut) in the tissue to enable the porous delivery member 54 and resection electrode to contact the tissue. Once tissue is cut or resected, as seen in FIG. 6C, the porous delivery member 54 may contact the exposed inner walls 104a, 104b of the tissue 100.

Figure 4:
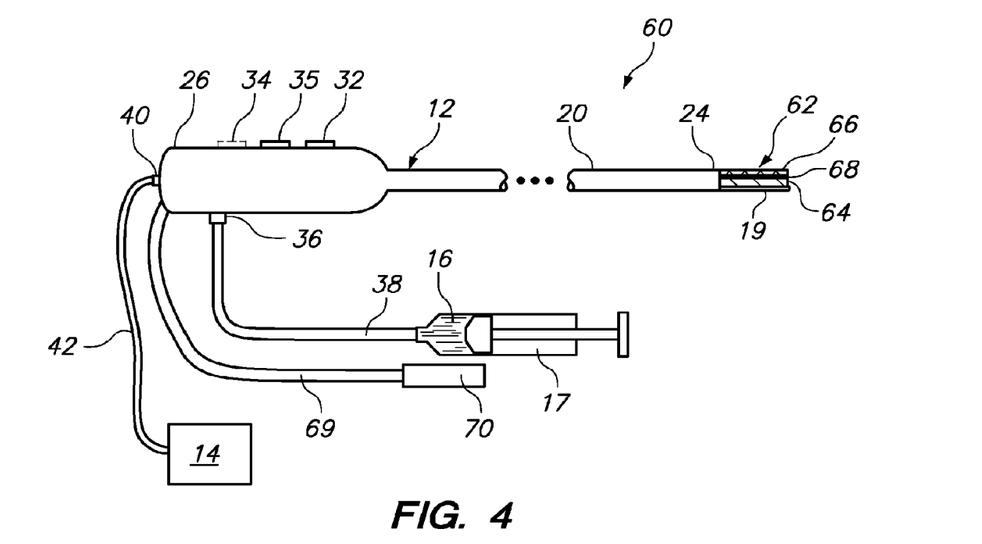
FIG. 4 is a plan view of a resection device according to another preferred aspect of the invention.
Figure 4A:
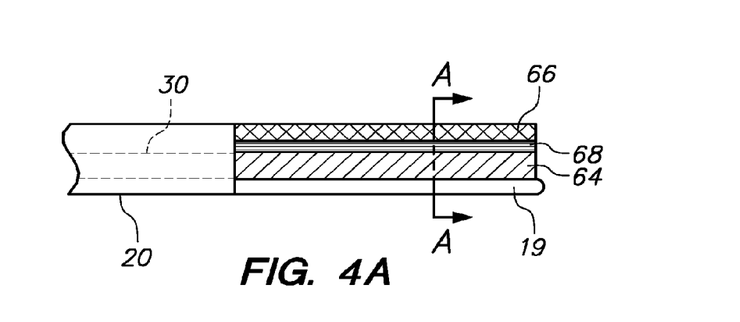
FIG. 4A is a magnified plan view of the distal end of the resection device illustrated in FIG. 4.
Figure 4B:
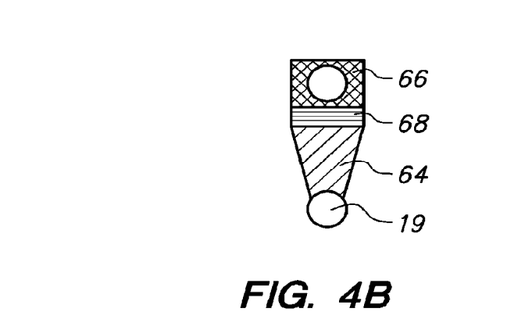
FIG. 4B is a cross-sectional view of the distal end of the resection device taken along the line A-A in FIG. 4A.

FIGS. 4, 4A, and 4B illustrate yet another embodiment of a resection probe 60 according to an alternative aspect of the invention. Those features of the resection probe 60 that are common with the embodiment illustrated in FIGS. 1, 1A, and 1B retain the same element number for sake of clarity. In the resection probe 60 of this embodiment, ultra-violet light is used to initiate or accelerate polymerization of the hemostasis-promoting material 16. The distal end 24 of the probe shaft 20 terminates in a tissue resection assembly 62. The assembly includes a resection electrode 19, a porous delivery member 64, an ultra-violet (UV) light emitter 66, and an ultra-violet light shield 68 interposed between the UV light emitter 66 and the porous delivery member 64.

The resection electrode 19 is RF-powered as described in detail herein. The porous delivery member 64 is fluidically coupled with conduit 30 in the probe shaft 20 as best seen in FIG. 4A. In this regard, the hemostasis-promoting material 16 is able to pass from conduit 30, into the porous delivery member 64, and onto the resected tissue. The porous delivery member 64 may be formed from a solid, porous material that is capable of weeping hemostasis-promoting material 16 on resected tissue. The porous delivery member 64 may also be formed from the same material used to form the porous delivery member 54 shown in FIGS. 3, 3A, and 3B.

The ultra violet light emitter 66 may be formed as a light pipe or other structure capable of emitting light in the radial direction (with respect to the long axis of probe 12). One or more reflective or refractive surfaces may be needed to alter the path of the light from a generally axial path (e.g., along the length of the probe shaft 20) to a direction that is generally perpendicular to the long axis of the probe 12. Alternatively, the ultra violet light emitter 66 may be formed from a fiber optic cable or bundle (not shown) that terminates in a mirrored or refractive surface to bend the light generally perpendicular to the long axis of the probe 12.

UV light may be emitted from the entire length of the light emitter 66. Alternatively, UV light may be directed radially outward at one or more points along the length of the light emitter 66. The UV light emitter 66 is coupled, for example, via fiber optic cables 69 or the like to a UV light source 70. The UV light source 70 may emit light over a range of UV wavelengths (e.g., a broadband source) or, alternatively, emit light at one or more discrete or predominant wavelengths.

The UV light shield 68 may be formed from any material impermeable to ultra-violet radiation. For example, an opaque material impermeable to all forms of light may be used. Alternatively, the light shield 68 may specifically prevent transmission of radiation in the UV wavelength range.

In one embodiment, the porous delivery member 64 may be formed having a generally triangular cross-sectional shape. For example, the resection electrode 19 may be formed at one apex of the porous delivery member 64 as is shown in FIG. 4B. In this orientation, the chance that stray UV light may enter the porous delivery member 64 is reduced or eliminated. If UV light entered the porous delivery member 64, then the hemostasis-promoting material 16 could potentially cure within the device 60 thereby occluding further flow. The outer or exposed surface of the porous delivery member 64 may optionally be coated with a UV-resistant coating to prevent UV light from penetrating deep within the porous delivery member 64.

Referring to FIG. 4, the handle assembly 26 may include an actuator 35 such as a button or the like that permits the selective release of UV light via the UV light emitter 66. In certain situations, the operator may want to apply or irradiate the cut tissue with UV light after performing a cutting or resection operation. In this case, a separate actuator 35 may be provided to trigger delivery of UV light. Alternatively, the same actuator or button 32 used to energize the resection electrode 19 may be used to trigger UV light. In this regard, UV light is delivered simultaneously with activation of the resection electrode 19. In yet another alternative, the actuator or button 34 used to deliver the polymerizable hemostasis-promoting material 16 may also be used to control or modulate UV light delivery.

Having described the general structure and function of the tissue resection devices (10, 15, 50, 60), their operation in resecting tissue will be described. As best seen in FIGS. 5A-5C the tissue 100 may be located anywhere in the body where resection may be beneficial. Most commonly, the tissue 100 will contain a solid tumor within an organ of the body, such as the liver, kidney, pancreas, breast, prostrate (not accessed via the urethra), and the like. In this case, an unhealthy tissue portion 100a, e.g., a cancerous portion containing a tumor, e.g., a lobe of a liver, may be resected from the healthy portion of the tissue 100b. It should be understood that the tissue resection devices (10, 15, 50, 60) may also be used to resect donor organ tissue such as, for example, the resection of donor liver tissue in a liver transplant surgery.

In the preferred method, access to the tissue 100 may be accomplished through a surgical opening to facilitate movement of the resection probe within the patient as well as to facilitate removal of the resected tissue 100a from the patient.

However, access to the tissue 100 may alternatively be provided through a percutaneous opening, e.g., laparoscopically, in which case, the tissue resection probe 12 can be introduced into the patient through a cannula, and the removed tissue 100a may be minsilated and aspirated from the patient through the cannula.

The operation of the RF-based tissue resection device (10, 50, 60) is now described in resecting unhealthy portion of tissue 100a to be removed from a patient, which has a tumor, from a healthy portion of tissue 100b to be retained within the patient. First, the RF generator 14 and associated cable 42 are connected to the electrical connector 40 on the handle 26, and the syringe 17 and associated tubing 38 are connected to the port 36 on the handle 26.

Next, the resection probe 12 is manipulated, such that the resection electrode 19 is moved in proximity to the tissue 100 along a resection line 102, and RF energy is conveyed between the RF generator 14 and the resection electrode 19. At the same time or prior to when RF energy is conveyed to the resection electrode 19, the syringe 17 is then operated such that the hemostasis-promoting material 16 is conveyed under positive pressure, through the tubing 38, and into the port 36. The hemostasis-promoting material 16 travels through the fluid conduit 30 within the probe shaft 20 and out the one or more ejection ports 28 (in the embodiments shown in FIGS. 1, 1A, 1B) or out the porous delivery members 54, 64 (in the embodiments shown in FIGS. 3, 3A, 3B, 4, 4A, and 4B).

In one method, the hemostasis-promoting material 16 travels onto the tissue resection member 18 where it then is passed or transferred to the tissue 100 in a subsequent cutting operation (described in more detail below). Alternatively, the hemostasis-promoting material 16 may pass directly from the resection probe 12 to the tissue 100.

As best seen in FIG. 5A, to resect or cut the tissue 100, electrical energy is conveyed from the resection electrode 19 through the tissue 100 along the resection line 102, thereby cutting or separating a portion of the tissue 100 that straddles the resection line 102. The probe 12 is typically moved along the resection line 102 in one or more strokes with each stroke cutting deeper within the tissue 100. The now formed cut may take the general cross-sectional shape of a "V" wherein the tissue 100 includes exposed walls or sides 104a, 104b that are formed as a result of the resecting operation.

As seen in FIG. 5A, the exposed walls or sides 104a, 104b of the tissue 100 are coated with a polymerizable hemostasis-promoting material 16. The hemostasis-promoting material 16 may be deposited onto the walls 104a, 104b at substantially the same time as the cutting or resecting operation is performed.

In one embodiment, the polymerizable hemostasis-promoting material 16 may be dispensed by a activation of a heat and/or current sensitive valve (not shown) that operates by the principle of thermal expansion, such as a concentric nozzle assembly made of dissimilar metals that is heated with the RF power on its way to the distal end 24 of the device 10. By heating the concentric assembly, and by virtue of differing thermal expansion of the metals, a gap may be generated in the concentric assembly. The pressurized polymer material 16 would then flow from the distal end 24.

Alternatively, the syringe 17 or other pumping mechanism may be engaged to coat the newly formed tissue walls 104a, 104b with the hemostasis-promoting material 16 after a cutting stroke or operation has taken place. After application of the hemostasis-promoting material 16, the material 16 cures or polymerizes. While the resecting electrode 19 has the ability to partially or even fully seal lumens via collagen shrinkage, there may be additional areas of tissue bleeding. These areas of bleeding, however, are rapidly sealed by the polymerizable hemostasis-promoting material 16.

The resection of the tissue 100 continues as is shown in FIGS. 5B and 5C. In FIG. 5B, a V-shaped groove or cut is shown fully across the resection line 102. As seen in FIG. 5B, the walls of the exposed tissue contains a film or is otherwise substantially coated with the polymerizable hemostasis-promoting material 16. As seen in FIGS. 5A, 5B, and 5C, a localized region 106 adjacent to the resected tissue 100 undergoes coagulation in response to the energy supplied via the resection electrode 19. The probe 12 continues to cut the tissue 100 deeper along the resection line 102 until the unhealthy portion of tissue 100a is completely separated from the healthy portion of tissue 100b. The unhealthy portion of tissue 100a can then be removed.

The curing of the hemostasis-promoting material 16 may be initiated or accelerated by application of heat and/or RF energy from the resection electrode 19. The heat may be applied directly to the hemostasis-promoting material 16 from the probe 12. Alternatively, in embodiments where the hemostasis-promoting material 16 is ejected along a trailing or lagging edge, heat retained in the cut tissue aids in initiating and/or accelerating polymerization. In still another alternative, curing of the hemostasis-promoting material 16 may be initiated or accelerated by application of radiation such as UV light from a probe 60 of the type illustrated in FIGS. 4, 4A, and 4B.

Figure 6A:
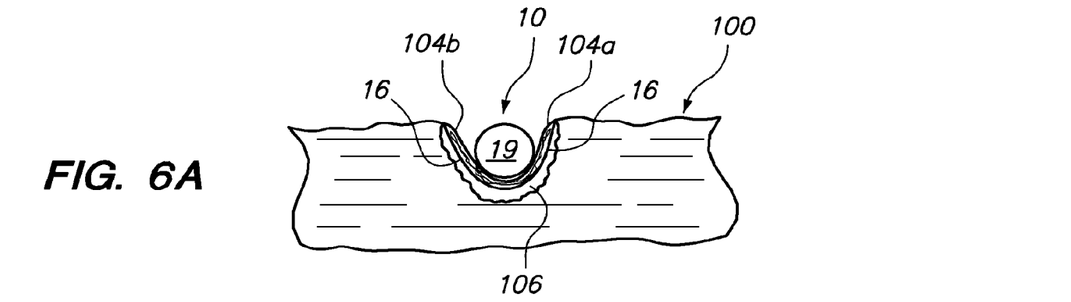
FIG. 6A is a cross-sectional view of a portion of tissue being resected using a resection probe according to one embodiment of the invention.
Figure 6B:
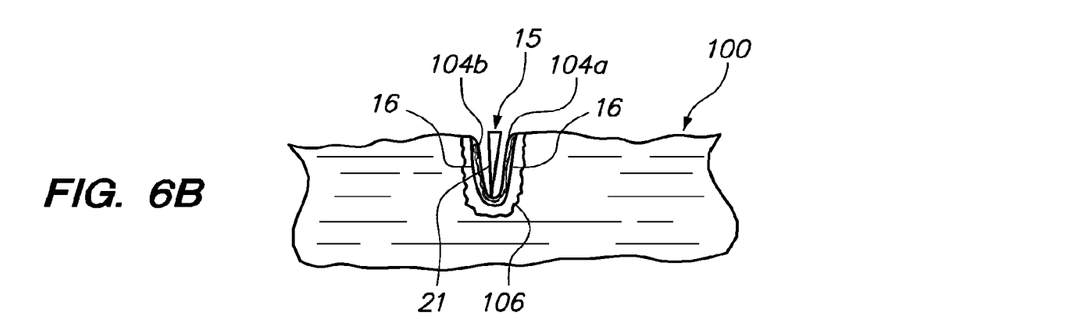
FIG. 6B is a cross-sectional view of a portion of tissue being resected using a resection probe according to another embodiment of the invention.
Figure 6C:
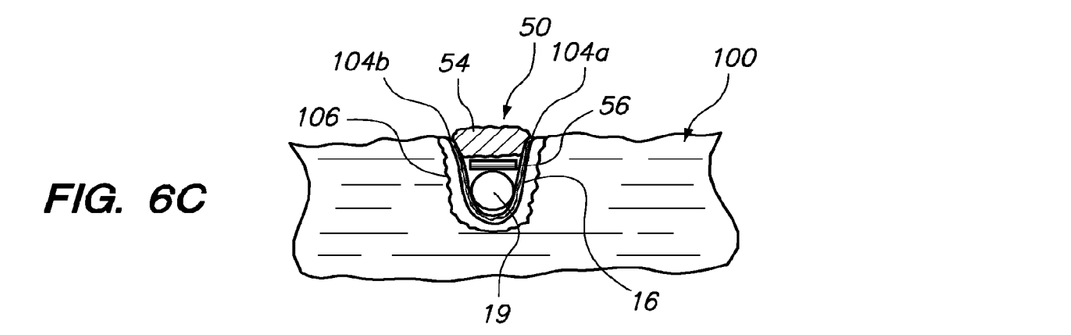
FIG. 6C is a cross-sectional view of a portion of tissue being resected using a resection probe according to another embodiment of the invention.

FIGS. 6A-6D illustrate cross-sectional views of the various resection probes (10, 15, 50, 60) resecting tissue 100. FIG. 6A illustrates the resection probe device 10, wherein the resection electrode 19 is used to resect tissue 100. FIG. 6A illustrates a layer or film of hemostasis-promoting material 16 disposed on the exposed walls 104a, 104b of the now-cut tissue 100. Also illustrated is a localized region of coagulated tissue 106 just underlying the layer or film of hemostasis-promoting material 16. FIG. 6B illustrates the resection probe device 15, wherein the mechanical resection member 21 is used to resect tissue 100.

FIG. 6C illustrates the resection probe 50 used to resect tissue 100. As seen in FIG. 6C, in certain embodiments of the invention, the porous delivery member 54 may be sized such that an exterior surface is able to directly contact the exposed walls 104a, 104b of the cut tissue 100. In this regard, the porous delivery member 54 is able to paint or apply hemostasis-promoting material 16 directly to the exposed tissue 104a, 104b. During delivery, the hemostasis-promoting material 16 may flow or even pool at the apex region where tissue cutting takes place. In this manner, the hemostasis-promoting material 16 is able to cover substantially all of the exposed tissue regions 104a, 104b.

Figure 6D:
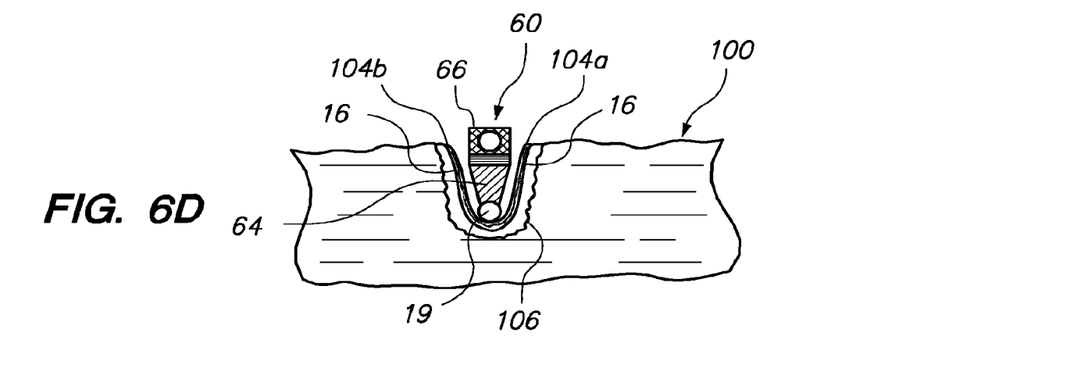
FIG. 6D is a cross-sectional view of a portion of tissue being resected using a resection probe according to another embodiment of the invention.

FIG. 6D illustrates the resection probe 60 used to resect tissue 100. The resection probe 60 in this embodiment uses UV light to initiate or accelerate the polymerization of the hemostasis-promoting material 16.

In another embodiment, the hemostasis-promoting material 16 may be dispensed from a forceps-type device (not shown) such as those used for open surgery or endoscopic surgery used for nodulectomies, lobectomy or volume reduction surgeries of the lung. The hemostasis-promoting material 16 will aid in hemostasis and air-leak sealing of the lung. The hemostasis-promoting material 16 may also be dispensed from a stapling device, and be activated by any of the means mentioned above.

While embodiments of the present invention have been shown and described, various modifications may be made without departing from the scope of the present invention.

The invention, therefore, should not be limited, except to the following claims, and their equivalents.

What is claimed is:

1. A resection device comprising:
   an elongated probe shaft;
   a tissue resection member disposed at a distal end of the elongated probe shaft, the tissue resection member having a cutting surface configured for being placed in contact with tissue;
   a porous delivery member disposed at the distal end of the elongated probe shaft, the porous delivery member coupled at a proximal end to a fluid conduit;
   a pumping source containing therein a polymerizable hemostasis promoting material, the pumping source coupled to the fluid conduit; and
   an insulating member interposed between the resection member and the porous delivery member.

2. The resection device of claim 1, wherein the polymerizable hemostasis-promoting material comprises a thermally-activated polymer.

3. The resection device of claim 1, wherein the polymerizable hemostasis-promoting material comprises a light-activated polymer.

4. The resection device of claim 3, wherein the polymerizable hemostasis-promoting material is activated upon exposure to ultraviolet light.

5. The resection device of claim 1, wherein the polymerizable hemostasis-promoting material comprises energy-activated polymer.

6. The resection device of claim 5, wherein polymerizable hemostasis-promoting material is activated upon exposure to radiofrequency (RF) energy.

7. The resection device of claim 1, wherein the tissue resection member comprises a resection electrode.

8. The resection device of claim 7, wherein the resection electrode and porous delivery member are in electrical contact in a bipolar arrangement.

9. The resection device of claim 7, wherein the resection device is configured in a monopolar arrangement.

10. The resection device of claim 1, wherein the porous delivery member comprises a sponge.

11. The resection device of claim 1, wherein the source of polymerizable hemostasis-promoting material is pressurized.

12. A resection device comprising:
    an elongated probe shaft having a proximal end and a distal end;
    a tissue resection assembly disposed at the distal end of the elongated probe shaft, the tissue resection assembly comprising a resection electrode and a porous delivery member separated from the resection electrode by an insulating member interposed between the resection electrode and the porous delivery member; and
    a pumping source containing therein a polymerizable hemostasis promoting material, the pumping source fluidically coupled to the porous delivery member.

13. The resection device of claim 12, wherein the polymerizable hemostasis-promoting material is activated upon exposure to ultraviolet light.

14. The resection device of claim 12, wherein the polymerizable hemostasis-promoting material comprises energy-activated polymer.

15. A resection device comprising:
    an elongated probe shaft having proximal end, a distal end, and a fluid conduit extending between the proximal end and the distal end;
    a tissue resection assembly disposed at the distal end of the elongated probe shaft, the tissue resection assembly comprising a resection electrode and a porous delivery member coupled to the fluid conduit;
    an insulating member disposed between the resection electrode and the porous delivery member, such that the insulating member electrically isolates the resection electrode from the porous delivery member; and
    a pumping source containing therein a polymerizable hemostasis promoting material, the pumping source coupled to the fluid conduit.

16. The resection device of claim 15, wherein the device is configured in a monopolar arrangement.

17. The resection device of claim 15, wherein the resection electrode and the porous delivery member are in electrical contact in a bipolar arrangement.

18. A resection device comprising:
    an elongated probe shaft having a fluid conduit disposed therein;
    a tissue resection electrode disposed at a distal end of the elongated probe shaft, the tissue resection electrode having a cutting surface configured for being placed in contact with tissue;
    a porous delivery member comprising an open-cell structure disposed at the distal end of the elongated probe shaft, the porous delivery member coupled at a proximal end one end of the fluid conduit;
    a syringe containing therein a polymerizable hemostasis promoting material, the syringe coupled to another end of the fluid conduit; and
    an insulating member interposed between the tissue resection electrode and the porous delivery member.

19. The resection device of claim 18, further comprising a RF generator electrically coupled to the tissue resection electrode.

20. The resection device of claim 19, wherein the RF generator is electrically coupled to the porous delivery member.

* * * * *